United States Patent [19]

Ameen et al.

[11] 4,358,627

[45] Nov. 9, 1982

[54] REDUCING CHLORIDE CONCENTRATION

[75] Inventors: Joseph G. Ameen, Apalachin; Charles A. Joseph, Endwell; Dennis L. Rivenburgh, Endicott; David W. Sissenstein, Endwell, all of N.Y.

[73] Assignee: International Business Machines Corporation, Armonk, N.Y.

[21] Appl. No.: 253,491

[22] Filed: Apr. 13, 1981

Related U.S. Application Data

[63] Continuation of Ser. No. 116,190, Jan. 28, 1980, abandoned.

[51] Int. Cl.$^3$ .................... C07C 19/00; C07C 21/00
[52] U.S. Cl. .................................................. 570/238
[58] Field of Search ...................................... 570/238

[56] References Cited

U.S. PATENT DOCUMENTS

| | | | |
|---|---|---|---|
| 2,852,572 | 9/1958 | Shuckys | 570/238 |
| 2,888,495 | 5/1959 | Kissling | 570/238 |
| 3,209,040 | 9/1965 | Daras et al. | 260/654 |
| 3,294,851 | 12/1966 | Robol et al. | 570/238 |
| 3,309,166 | 3/1967 | Moncada | 8/142 |
| 3,452,110 | 6/1969 | Cooley et al. | 260/654 |
| 3,691,239 | 9/1972 | Hackett et al. | 570/238 |
| 3,751,494 | 8/1973 | Beckers | 570/238 |
| 3,801,659 | 4/1974 | Dahlberg et al. | 570/238 UX |
| 3,862,900 | 1/1975 | Reusser | 570/238 |
| 4,080,393 | 3/1978 | Deselaers et al. | 570/238 |

*Primary Examiner*—Paul F. Shaver
*Attorney, Agent, or Firm*—Pollock, Vande Sande & Priddy

[57] ABSTRACT

A process for reducing the chloride concentration in a system which contains an ethylenically unsaturated chlorinated hydrocarbon, water and HCl which includes providing certain nitrogen-containing compounds in the system and contacting the system with a molecular sieve. The process surprisingly is capable of regenerating the nitrogen-containing compounds employed.

19 Claims, No Drawings

REDUCING CHLORIDE CONCENTRATION

This is a contination of application Ser. No. 116,190, filed Jan. 28, 1980, now abandoned.

DESCRIPTION

Technical Field

The present invention is concerned with reducing the concentration of chloride in a system which contains HCl, water, and an ethylenically unsaturated chlorinated hydrocarbon. In particular, the present invention is concerned with reducing the chloride content in those compositions which also contain a nitrogen-containing compound of the type that has at least one unshared pair of electrons capable of forming a dative covalent bond. The present invention is especially advantageous in those systems which are used in contact with electronic components such as module substrates, assemblies, and printed circuit boards.

BACKGROUND ART

Certain ethylenically unsaturated chlorinated hydrocarbons such as perchloroethylene are employed for cleaning and degreasing electronic components such as module substrates, assemblies, and printed circuit boards. However, at the operating temperature, such hydrocarbons such as perchloroethylene tend to react with water and/or oxygen contaminants to produce, in the case of perchloroethylene, trichloroacetyl chloride which may then subsequently hydrolize to hydrochloric acid.

The presence of chloride can be extremely harmful to the components contacted with the compositions. For instance, chloride can be very detrimental to circuitry resulting in "black fingers" on electrical contacts and thereby contributing to electrolytic corrosion on metalized ceramics. The term "black fingers" refers to corrosion of for instance tin and/or lead on the ceramic resulting in the corresponding chlorides.

In order to remove chloride from such systems, nitrogen containing inhibitors such as diallylamine have been added. The nitrogen compound such as the diallylamine is generally added periodically in order to combine with for instance the intermediate trichloroacetyl chloride and also with the by-product, hydrochloric acid.

Reactions nos. 2 and 3 hereinbelow illustrate the reactions when adding diallylamine to a perchloroethylene system:

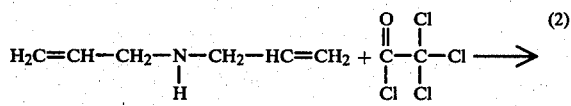

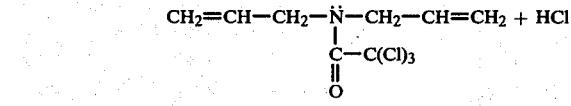

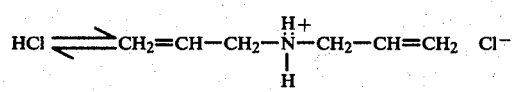

The diallylamine hydrochloride formed from reaction Nos. 3, illustrated above is an insoluble precipitate in the perchloroethylene and it can thereby be removed in filters. However, it is still present in the system and is in equilibrium therein. If the filters are not changed periodically, more and more of the nitrogen compound (e.g. diallylamine) is needed to control the chloride concentration. Various different processes have been suggested for purifying liquids such as perchlorethylene to remove certain impurities therein.

For instance, U.S. Pat. No. 3,751,494 is concerned with removing saturated partially-chlorinated hydrocarbons from unsaturated chlorocarbon and chlorinated hydrocarbons including perchlorethylene by treatment with a type 13X molecular sieve. The partially-chlorinated hydrocarbons are dechlorinated and the products of dehydrochlorination are at least partially adsorbed. In the process suggested in U.S. Pat. No. 3,751,494, the action of the molecular sieve on the saturated chlorinated hydrocarbons also results in the production of hydrogen chloride.

U.S. Pat. No. 2,888,495 to Kissling suggests purifying perchloroethylene by contacting it with ion exchange resins in order to reduce the acidity of the perchlorethylene composition. U.S. Pat. No. 3,309,166 to Moncada et al. suggests an adsorption for purifying various solvents among which is suggested perchlorethylene. U.S. Pat. No. 3,452,110 is exemplary of those patents which suggest filtering processes for purifying solvents including perchloroethylene.

DISCLOSURE OF INVENTION

The present invention is concerned with a process for reducing the concentration of chloride in a system which contains an ethylenically unsaturated chlorinated liquid hydrocarbon and HCl. The process comprises providing in the system with the ethylenically unsaturated chlorinated hydrocarbon a nitrogen-containing compound. The nitrogen-containing compound must have at least one unshared pair of electrons which are capable of forming a dative covalent bond. The system which contains the nitrogen-containing compound is contacted with a molecular sieve to thereby reduce the concentration of chloride in the system. The molecular sieve preferably has an effective pore size of about 3 to about 10 angstroms.

A dative bond, also known as a semipolar bond or coordinate covalence, is a covalent bond in which one atom has supplied both electrons thus giving rise to a difference in charge of one electron between two atoms in the same molecule.

DESCRIPTION OF BEST AND VARIOUS MODES FOR CARRYING OUT INVENTION

The ethylenically unsaturated chlorinated hydrocarbons which are processed according to the present invention are liquid at the conditions of treatment and preferably liquid at normal room temperatures. In addition, the chlorinated hydrocarbons processed according to the present invention are preferably mono-ethylenically unsaturated. Examples of some ethylenically unsaturated chlorinated hydrocarbons are trichloroethylene, perchloroethylene, hexachloropropylene, and hexachlorobutadiene. Ethylenically unsaturated chlorinated hydrocarbons as exemplified by perchloroethylene under conditions of elevated temperatures tend to react with water and/or oxygen contaminants to produce intermediates such as trichloroacetyl chloride in the case of perchloroethylene, which in turn may then hydrolize to hydrochloric acid as exemplified by the following reaction sequence:

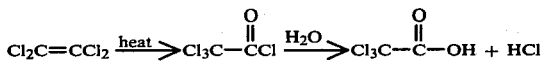

The compositions treated according to the present invention contain water.

The nitrogen-containing compounds which are employed in the process of the present invention must have a pair of shared electrons which are capable of forming a dative covalent bond. The nitrogen compounds employed in the present invention are generally low molecular weight nitrogen compounds which are liquid and are soluble in the ethylenically unsaturated chlorinated hydrocarbon and include primary and secondary amines. The nitrogen compounds usually have molecular weights up to about 500. Examples of some nitrogen compounds suitable for the present invention are diallylamine, diethylamine, dimethylamine, and diacetyl amine. The preferred amine employed according to the present invention is diallyamine. Some of the amines can be represented by the formula:

$$RR_1NH$$

wherein R is alkanoyl or aroyl or hydrocarbyl such as alkyl, allyl, cycloalkyl, and aryl; and $R_1$ is H, or alkanoyl or aroyl or hydrocarbyl such as alkyl, allyl, cycloakyl, and aryl. The number of carbon atoms of the above groups being selected so that the amine is a liquid and has a molecular weight of about 500 or less.

For illustration purposes, using diallylamine and perchloroethylene, the following reactions are believed to occur;

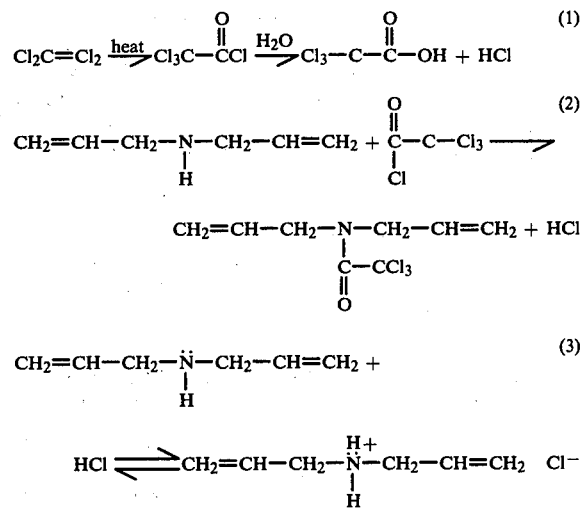

The diallylamine hydrochloride prepared from reaction No. 3 above is an insoluble precipitate in perchloroethylene and is taken out in filters. However, it is still present in the system and is in equilibrium therein. Since there is an equilibrium reaction, chloride will still be present in the system to some extent.

In order, to overcome this particular problem, it has been found according to the present invention that contact of the above system with a molecular sieve will result in reduction of the concentration of chloride in the system. The molecular sieves employed preferably have an effective pore size of about 3 to about 10 angstroms. Molecular sieves are crystalline metal aluminosilicates.

The molecular sieves are basically a 3-dimensional framework of $SiO_4$ and $AlO_4$ tetrahedra. The tetrahedra being cross-linked by the sharing of oxygen atoms so that the ratio of oxygen atoms to the total of the aluminum and silicon atoms is equal to 2. The electro valance of the tetrahedra containing aluminum is balanced by the inclusion in the crystal of a cation, for example an alkali or alkaline earthmetal ion. One cation may be exchanged for another by ion exchange techniques which are known. The spaces between the tetrahedra are occupied by water molecules prior to dehydration. The dehydration results in crystals interlaced with channels of molecular dimensions that offer very high surface areas for the adsorption of foreign molecules. In addition, the term "molecular sieve" as used in the present disclosure contemplates not only aluminosilicates, but also substances in which the aluminum has been partly or wholly replaced, such as for instance by gallium and/or other metal atoms, and further includes substances in which all or part of the silicon has been replaced, such as for instance by germanium. Titanium and zirconium substitution may also be practiced.

Most molecular sieves, or zeolites as they are also referred to, are prepared or occur naturally in the sodium form, so that sodium cations are associated with the electro negative sites in the crystal structure. However, the molecular sieve may be ion exchanged. Suitable cations for replacement of sodium in the molecular sieve crystal structure include ammonium (decomposable to hydrogen), hydrogen, rare earth metals, alkaline earth metals, and the like. Various suitable ion exchange procedures and cations which may be exchanged into crystal structure are well known to those skilled in the art.

Examples of the naturally occurring crystalline aluminosilicate zeolites which may be used or included in the present invention are faujasite, mordenite, clinoptilote, chabazite, analcite, erionite, as well as levynite, dachiardite, paulingite, noselite, ferriorite, heulandite, scolccite, stibite, harmotome, phillipsite, brewsterite, flarite, datolite, gmelinite, caumnite, leucite, lazurite, scaplite, mesolite, ptholite, nepheline, matrolite, offretite and sodalite.

Examples of the synthetic alumino-silicate zeolites which are useful for carrying out the present invention are Zeolite X, U.S. Pat. No. 2,882,244, Zeolite Y, U.S. Pat. No. 3,130,007; and Zeolite A, U.S. Pat. No. 2,882,243; as well as Zeolite B, U.S. Pat. No. 3,008,803; Zeolite D, Canada Pat. No. 661,981; Zeolite E, Canada Pat. No. 614,495; Zeolite F, U.S. Pat. No. 2,996,358; Zeolite H, U.S. Pat. No. 3,010,789; Zeolite J, U.S. Pat. No. 3,001,869; Zeolite L, Belgian Pat. No. 575,177; Zeolite M, U.S. Pat. No. 2,995,423, Zeolite O, U.S. Pat. No. 3,140,252; Zeolite Q, U.S. Pat. No. 2,991,151; Zeolite S, U.S. Pat. No. 3,054,657, Zeolite T, U.S. Pat. No. 2,950,962; Zeolite W, U.S. Pat. No. 3,012,853, Zeolite Z, Canada Pat. No. 614,495; and Zeolite Omega, Canada Pat. No. 817,915. Also ZK-4HJ, alpha beta and ZSM-type zeolites are useful. Moreover, the zeolites described in U.S. Pat. Nos. 3,140,249, 3,140,253, 3,044,482 and 4,137,151 are also useful, the disclosures of said patents being incorporated herein by reference.

The preferred molecular sieves employed according to the present invention are those commercially available from Union Carbide under the trade designations Lindy Molecular sieves types 3A,4A,5A and 13X and most preferably the so-called acid resistent sieves, types AW300 and AW500. The effective pore size of these preferred molecular sieves are as follows:

| Type | Pore Size |
| --- | --- |
| 3A | 3Å |
| 4A | 4Å |
| 5A | 5Å |
| 13X | 10Å |
| AW300 | 4Å |
| AW500 | 5Å |

Such are available as pellets of about ⅛" or 1/16" diameter. A discussion of the acid resistent molecular sieve Types AW-300 and AW-500 can be found in the Oil and Gas Journal, Dec. 2, 1963, A Report On Acid-Resistent Molecular Sieve Types AW-300 and AW-500 by J. J. Collins, disclosures which is incorporated here by reference. In addition, a discussion of Lindy molecular sieve type 3A, Lindy molecular sieve type 4A, Lindy molecular sieve type 5A, and Lindy molecular sieve type 13X can be found in Lindy molecular sieves adsorbent data circulars F-21B, F-3996, F-37, and F-23A respectively from Union Carbide Corporation. In addition, the preferred molecular sieves employed according to the present invention are alkali metal aluminosilicates synthetic molecular sieves.

The molecular sieves employed adsorb onto the sieve some nitrogen compound such as the diallylamine but since the molecular sieve has a much greater affinity for water then for other materials as is well known, the water after being adsorbed to some minimum extent then tends to replace the nitrogen compound on the sieve. Since the presence of water produces chlorides and since water tends to replace the nitrogen compound on the sieve, especially under conditions of relatively high humidity, the presence of water in the system releases diallylamine to react with excess chloride.

Moreover, the molecular sieve besides being a water scavenger is also a hydrochloric acid scavenger. By adsorbing hydrochloric acid, it shifts the equilibrium in reaction No. 3 described herein above to the left thereby forming in the case of diallylamine hydrochloride, diallylamine and HCl. As HCl is produced, it is adsorbed until all of the diallylamine hydrochloride is broken down to diallylamine and HCl. It is surprising that the cleavage due to contact with the molecular sieve results in producing HCl since usually such compounds cleave or break at the bond between the H and Cl of the HCl portion of the molecule.

In addition, since nitrogen compound such as in the form of a chloride complex is removed from prior systems which do not employ a molecular sieve, the prior systems must periodically be replenished with newly added nitrogen compound. However, the present invention surprisingly results in the regeneration of the nitrogen compound and reintroduction of it into the solution when released from the molecular sieve. Accordingly, the present invention makes it possible to maintain the desired level of nitrogen compound in the system without the necessity of replenishing the system with additional fresh nitrogen compound. Of course, if desired fresh nitrogen compound can be added in the practice of the present invention. According to the present invention, the compositions contain about 10 to about 150 ppm of the nitrogen compound and preferably about 50 to 100 ppm. This is a significant improvement over the use of the nitrogen compound such as the diallylamine in prior systems since such required about 200 to about 300 ppm.

The present invention makes it possible to provide compositions after contact with the molecular sieve which contain less than about 5 ppm and preferably less than about 1 ppm of chloride and less than 50 ppm and preferably less than 10 ppm of water. Without the use of the molecular sieve, prior processes resulted in about 2 to about 5 ppm of chloride and up to about 130 ppm of water and never below about 20 ppm of water.

In addition, prior processes which merely employed the nitrogen compound required a distillation in order to remove as much of the water as possible. However, the present invention does not require the use of a distillation step but can use such, if so desired, prior to adding the nitrogen compound.

The present invention can be practiced by contacting the composition with a fixed bed of the molecular sieve and at the present time is carried out by flowing the composition up through the bottom of the molecular sieve in a suitable vessel and out the top of the vessel. The vessel for a typical 500 to 800 gallon treatment system contains about 150 pounds of molecular sieve as a column about 4 feet high and 2 feet in diameter. The flow rate of the composition is about 1.2±0.2 gallons per minute and at present time the molecular sieve is regenerated about every eight hours. However, it is believed that once a week would be sufficient for regenerating the molecular sieve. A typical system for treating about 15 gallons of liquid employs about 700 grams of molecular sieve with a flow rate of about 0.75-1 gals./min. The molecular sieve is present as a column about 10 inches high and about 4 inches in diameter.

Although the acid resistent molecular sieves are preferred according to the present invention, because of the presence of chloride in the system, such is not entirely necessary in view of the small amount of chloride, the detrimental effect on the molecular sieve using those that are not specifically designated as acid resistent is minimal.

The compositions processed according to the present invention are generally at temperatures of about normal room temperature to about 121° C., with the lower temperatures being preferred since at the lower temperatures, increased amounts of water are adsorbed by the molecular sieve.

The compositions treated according to the present invention are preferably substantially, if not completely free of any saturated chlorinated hydrocarbons.

The following non limiting example is hereby presented to further illustrate the present invention.

EXAMPLE

About two liters of perchloroethylene containing diallylamine are added to a four neck flask having a thermometer inserted through one neck, connected to a condenser via another neck and being in contact with a heating element. The perchloroethylene is refluxed for about one hour at 100°–121° C. The perchloroethylene is then circulated by use of a pump out of the flask via a third neck and through an empty column and then back into the flask via the fourth neck. The perchloroethylene is circulated through conduits which are connected to two of the necks of the flask fitted with stoppers containing apertures for receiving the conduits. The column is then filled with about 50 grams of molecular sieve, Lindy type 4A, $\frac{1}{8}$" pellets and the perchloroethylene is then recirculated for another hour. The samples for two different runs are analyzed both before and after the presence of the molecular sieve for water, diallylamine, and chloride. The results are reproduced herein:

| Run 1 | |
|---|---|
| Without molecular sieve | |
| After reflux and circulation | |
| $H_2O$ | 343 ppm |
| diallylamine | 20 ppm |
| $Cl^-$ | 3.2 ppm |
| With molecular sieve | |
| $H_2O$ | 22 ppm |
| diallylamine | 74 ppm |
| $Cl^-$ | 1.7 ppm |
| Run 2 | |
| Without molecular sieve | |
| After reflux and circulation | |
| $H_2O$ | 22 ppm |
| diallylamine | 248 ppm |
| $Cl^-$ | <1 ppm |
| With molecular sieve | |
| $H_2O$ | 5 ppm |
| diallylamine | 158 ppm |
| $Cl^-$ | <1 ppm |

The above example clearly shows the effectiveness of the molecular sieve on reducing the chloride concentration and increasing the diallylamine concentration after sufficient diallylamine hydrochloride has been broken down into diallylamine and HCl and the HCl absorbed by the molecular sieve.

What is claimed is:

1. A process for reducing the concentration of chloride in a system consisting essentially of ethylenically unsaturated chlorinated hydrocarbon which is liquid at the conditions of the process, water and HCl which comprises providing in the system with said ethylenically unsaturated chlorinated hydrocarbon a nitrogen containing compound having at least one unshared pair of electrons capable of forming a dative covalent bond and contacting said system, subsequent to providing in the system said nitrogen compound, with a molecular sieve having an effective pore size of about 3 to about 10 Å to thereby reduce the concentration of chloride in said system after contact with said molecular sieve to less than 5 ppm and wherein said concentration of water after contact with said molecular sieve is less than 50 ppm and wherein said nitrogen containing compound forms a complex with HCl, said complex is broken down into HCl and said nitrogen containing compound upon contact with said molecular sieve thereby regenerating said nitrogen containing compound, wherein some nitrogen containing compound is adsorbed on the molecular sieve and is then replaced on said molecular sieve by water whereby said nitrogen containing compound is released back into said system.

2. The process of claim 1 wherein said hydrocarbon includes perchloroethylene.

3. The process of claim 1 wherein said nitrogen containing compound is a primary or secondary amine.

4. The process of claim 1 wherein said nitrogen containing compound is diallylamine.

5. The process of claim 1 wherein said hydrocarbon is perchloroethylene and said nitrogen containing compound is diallylamine.

6. The process of claim 1 wherein said nitrogen containing compound has a molecular weight up to about 500.

7. The process of claim 1 or 5 wherein said molecular sieve is of the type A or the type X.

8. The process of claim 1 or 5 wherein said molecular sieve is an acid resistent molecular sieve.

9. The process of claim 1 or 5 wherein said molecular sieve has an effective pore size of about 4 angstroms.

10. The process of claim 1 or 5 wherein said molecular sieve has a pore size of about 5 angstroms.

11. The process of claim 1 wherein the system is at temperatures of about normal room temperature to about 121° c. when contacted with said molecular sieve.

12. The process of claim 1 wherein the amount of said nitrogen compound employed in said system is about 10 to about 150 ppm.

13. The process of claim 1 wherein the amount of said nitrogen compound in said system is about 50 to about 100 ppm.

14. The process of claim 1 wherein the concentration of chloride after contact with said molecular sieve is less than 1 ppm, and the concentration of water after contact with said molecular sieve is less than 10 ppm of water.

15. The process of claim 1 wherein said chlorinated hydrocarbon is liquid at normal room temperatures and is monoethylenically unsaturated.

16. The process of claim 1 wherein said chlorinated hydrocarbon is selected from the group of trichloroethylene, perchloroethylene, hexachloropropylene or hexachlorobutadiene.

17. The process of claim 1 wherein said molecular sieve is of the type A or the type AW.

18. The process of claim 1 wherein said molecular sieve has an effective pore size of about 3 to about 5 Å.

19. The process of claim 17 or 18 wherein said molecular sieve is an acid resistent molecular sieve.

* * * * *

UNITED STATES PATENT AND TRADEMARK OFFICE
CERTIFICATE OF CORRECTION

PATENT NO. : 4,358,627
DATED : November 9, 1982
INVENTOR(S) : Ameen, et al.

It is certified that error appears in the above—identified patent and that said Letters Patent is hereby corrected as shown below:

Column 1, line 57, please delete "N̈" and insert therefor --- N ---.

Column 1, line 63, please delete "N" and insert therefor --- N̈ ---.

Signed and Sealed this

Twenty-second Day of March 1983

[SEAL]

Attest:

GERALD J. MOSSINGHOFF

Attesting Officer — Commissioner of Patents and Trademarks